(12) United States Patent
Messersmith et al.

(10) Patent No.: US 9,034,829 B1
(45) Date of Patent: May 19, 2015

(54) PH-SENSITIVE POLYMER-DRUG CONJUGATES FOR TARGETED DELIVERY OF THERAPEUTICS

(71) Applicant: Northwestern University, Evanston, IL (US)

(72) Inventors: Phillip B. Messersmith, Clarendon Hills, IL (US); Jing Su, Chicago, IL (US); Vincent L. Cryns, Deerfield, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 13/663,114

(22) Filed: Oct. 29, 2012

Related U.S. Application Data

(60) Provisional application No. 61/552,244, filed on Oct. 27, 2011.

(51) Int. Cl.
  *A61K 47/48* (2006.01)
  *A61K 31/69* (2006.01)
  *A61K 47/18* (2006.01)

(52) U.S. Cl.
  CPC ........... *A61K 47/48246* (2013.01); *A61K 31/69* (2013.01); *A61K 47/183* (2013.01)

(58) Field of Classification Search
  None
  See application file for complete search history.

(56) References Cited

U.S. PATENT DOCUMENTS

| | | | |
|---|---|---|---|
| 6,806,284 B1* | 10/2004 | Moser ........................... | 514/410 |
| 2003/0087338 A1* | 5/2003 | Messersmith et al. ....... | 435/68.1 |
| 2005/0106658 A1* | 5/2005 | DeFrees et al. .............. | 435/68.1 |
| 2006/0009550 A1* | 1/2006 | Messersmith et al. .......... | 524/17 |
| 2006/0127310 A1* | 6/2006 | Russell-Jones et al. ..... | 424/1.49 |
| 2010/0226855 A1* | 9/2010 | Nangia et al. ................. | 424/9.1 |

FOREIGN PATENT DOCUMENTS

| WO | WO 2009/002993 | * 12/2008 | ............. C07K 16/00 |
|---|---|---|---|

OTHER PUBLICATIONS

Liu et al. (Blood, 112: 3835-3846, 2008).*
Gunawan et al. (Langmuir, 23: 10635-10643, 2007).*
He, Lihong et al. "pH responsive self-healing hydrogels formed by boronate-catechol complexation", Chem. Commun., 2011, 47, 7497-7499.
Adams, Julian et al. "Potent and Selective Inhibitors of the Proteasome: Dipeptidyl Boronic Acids", Biorganic & Medicinal Chemistry Letters, 1998, 8, 333-338.
Groll, Michael et al. "Crystal Structure of the Boronic Acid-Based Proteasome Inhibitor Bortezomib in Complex with the Yeast 20S Proteasome", Structure 14, 2006, 14, 451-456.
James, Tony et al. "Novel Saccharide-Photoinduced Electron Transfer Sensors Based on the Interaction of Boronic Acid and Amine", Journal of the Amerrican Chemical Society, 1995, 117, 8982-8987.
James, Tony et al. "Saccharide Sensing with Molecular Receptors Based on Boronic Acid", Angew. Chem. Int. Ed. Engl., 1996, 35, 1910-1922.
James, Tony et al. "Chrial discrimination of monosaccharides using a fluorescent molecular sensor", Letters to Nature, vol. 374, 1995, 345-347.
Su, Jing et al. "Catechol Polymer for pH-Responsive, Targeted Drug Delivery to Cancer Cells", Journal of the American Chemical Society, 2011, 133(31), 18850-11853.
Kong, Yali et al. "Structure-Based Discovery of a Boronic Acid Biosostere of Combretastin A-4", Chemistry & Biology, 2005, 12, 1007.
Lee, Eun Seong et al. "Recent progess in tumor pH targeting nanotechnology", Journal of Controlled Release, 2008, 132, 164.
Lorand, John et al. "Polyol Complexes and Structure of the Benzeneboronate Ion", The Journal of Organic Chemistry, 1959, 24, 769.
Minkkila, Anna et al. "Discovery of Boronic Acids as Novel and Potent Inhibitors of Fatty Acide Amide Hydrolase", Journal of Medicinal Chemistry, 2008, 51, 7057.
Mohler, Linda K., et al. "Alpha-Amino Acid Chelative Complexation by an Arylboronic Acid", Journal of the American Chemical Society, 1993, 115, 7037.
Paugam, Marie-France et al. "Facilitated Catecholamine Transport through Bulk and Polymer-Supported Liquid Membranes", Journal of the American Chemical Society, 1996, 118, 9820.
Riggs, Jennfer A., et al. "Nucleotide Carrier Mixture with Transport Selectivity for Ribonucleoside-5'-phosphates", Tetrahedron Letters, vol. 37, No. 35, 6303-6306, 1996.
Roberts, Meredith et al. "Dynamically Restructuring Hydrogel Networks Formed with Reversible Covalent Crosslinks", Advanced Materials, 2007, 19, 2503-2507.
Springsteen, Greg et al. "A detailed examination of boronic acid-diol complexation", Tetrahedron 2002, 58, 5291-5300.
Torchilin, Vladimir et al. "Peptide and protein drug delivery to and into tumors: challenges and solutions", Drug Discovery Today, 2003, vol. 8, No. 6, 259-266.
Veronese, Francesco et al. "PEGylation, successful approach to drug delivery", Drug Discovery Today, 2005, vol. 10, No. 24, 1451-1458.
Winblade, Natalie et al. "Sterically blocking adhesion of cells to biological surfaces with a surface-active copolymer containing poly-(ethylene glycol) and phenylboronic acid", Biomed. Mater. Res., 2002, 59, 618-631.
Yan, Jun et al. "The relationship among pKa, pH, and binding constants in the interactions between boronic acids and diols—it is not as simple as it appears", Tetrahedrom, 2004, 60, 11205.
Yang, Wengian et al. "Boronic Acid Compounds as Potential Pharmaceutical Agents", Medicinal Research Reviews, 2003, 23, 346.

* cited by examiner

*Primary Examiner* — Brad Duffy
*Assistant Examiner* — Nelson B Moseley, II
(74) *Attorney, Agent, or Firm* — Reinhart Boerner Van Deuren s.c.

(57) ABSTRACT

Polymeric delivery systems for boronic acid-containing therapeutics, related compounds and methods of use, for a pH-sensitive chemoselective approach to delivery of such a therapeutic.

5 Claims, 12 Drawing Sheets

Figure 1:
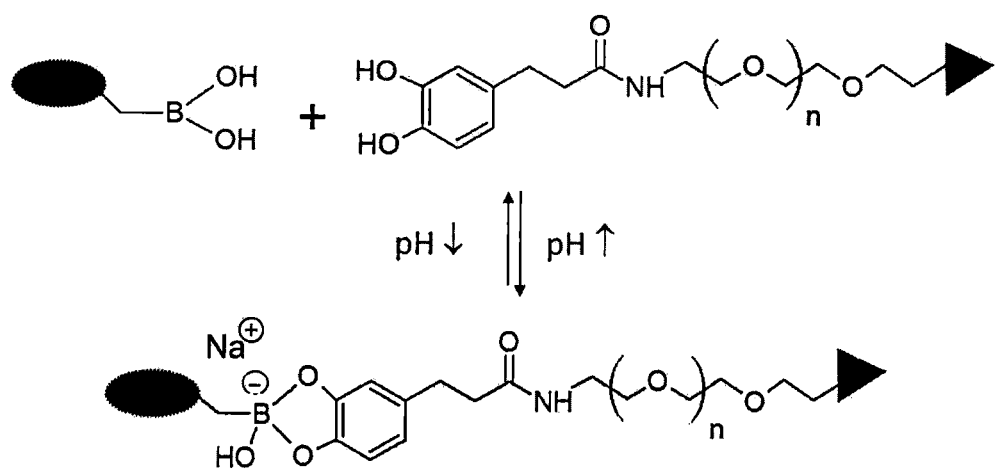

Figure 5A
Figure 5B
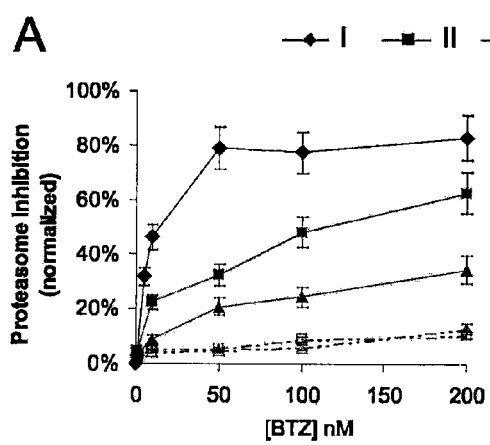
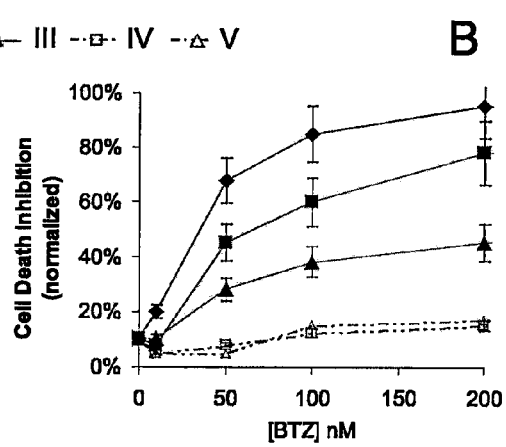
C  Half-Maximal Inhibitory Concentrations (IC$_{50}$, mean ± standard deviation) of free BTZ, BPC-BTZ and BPC
| IC$_{50}$ (nM) | BTZ | BPC-BTZ | BPC |
|---|---|---|---|
| Vector | 8.3 ± 1.5 | 29.0 ± 3.3 | > 1000 |
| H-Ras V12 | 7.9 ± 0.9 | 13.2 ± 2.1 | ND |
Figure 5C Figure 7A
Figure 7B
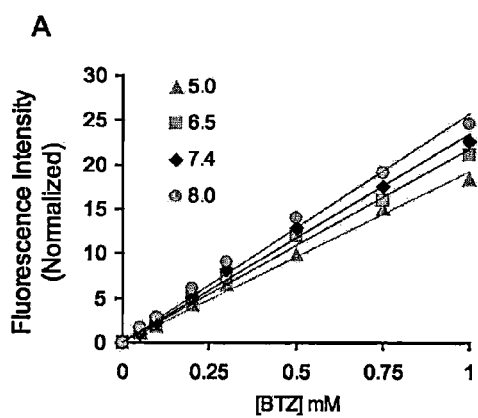
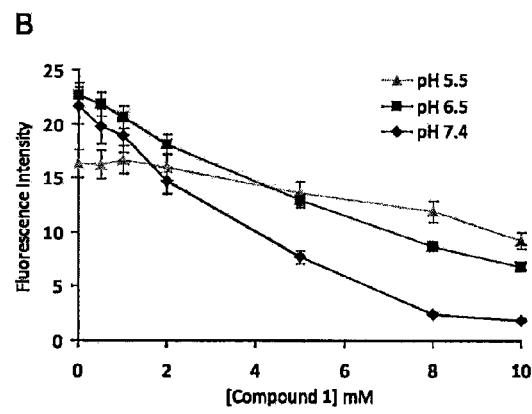

Figures 8A-D
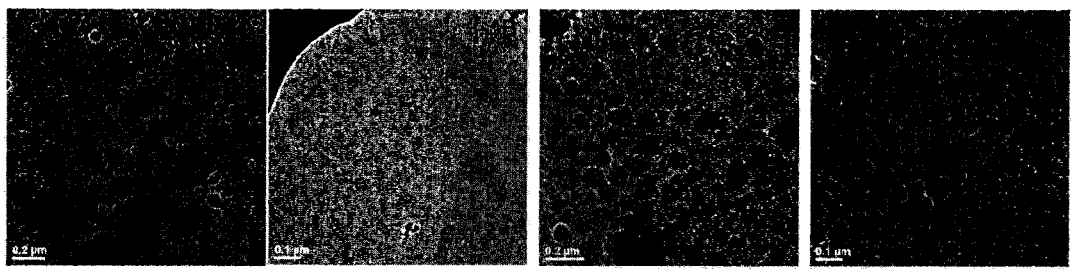

PH-SENSITIVE POLYMER-DRUG CONJUGATES FOR TARGETED DELIVERY OF THERAPEUTICS

This application claims priority benefit of application Ser. No. 61/552,244 filed Oct. 27, 2011—the entirety of which is incorporated herein by reference.

This invention was made with government support under grant number R37DE014193 awarded by the National Institutes of Health. The government has certain rights in the invention.

BACKGROUND OF THE INVENTION

Targeted drug delivery systems aim to improve efficacy and reduce toxicity of potent therapeutics in treatment of a variety of diseases. For example, chemotherapy is one of the major treatments for cancers but is linked with life-threatening side effects because of its toxicity on healthy proliferating cells and relation to multi-drug resistance against anticancer drugs. Tumor-targeting delivery systems have been developed to alter the biodistribution of drugs, aiming to achieve drug accumulation in cancer tissue through enhanced permeability and retention (EPR) effect and/or specific cell surface recognition.

On the other hand, controlled drug release at pathological tissues is desired to maintain the expected therapeutic properties of any delivered potent agent. Conventional delivery systems for anti-cancer drugs utilize biodegradation of materials that encapsulate the drugs, either time-dependent manner or through environmentally triggered mechanisms. For example, the extracellular pH in tumor tissue is slightly lower than that in the normal tissue, which has been used to develop acidity-triggered drug release at tumor tissue. (See, e.g., Lee, E. S.; Gao, Z.; Bae, Y. H. J Control Release 2008, 132, 164). In addition, the significantly increased acidity in endosomes and lysosomes in cells also enables the use of low pH-initiated release of drugs from endocysed drug carriers as a complementing approach to increase the interacting efficacy of drugs with their intracellular targets. (Torchilin, V. P.; Lukyanov, A. N. Drug Discov Today 2003, 8, 259-266).

Boronic acids are capable of forming covalent linkages with 1,2-, or 1,3-dihydroxyl (diol) structures to give boronate esters. Dissociation constants of boronate esters in aqueous solutions have been reported in the micromolar range, (Lorand, J. P.; Edwards, J. O. The Journal of Organic Chemistry 1959, 24, 769) and the stabilities of these esters are dependent upon factors such as pH and buffer formulation. In particular, the covalent association between boronic acid and diol moieties gives stable boronate conjugates in aqueous solutions at neutral and basic pH, while acidic pH triggers dissociation of boronate esters to release free boronic acid from the diol. This dynamic association-dissociation process has been systematically studied from the perspective of boronic acid and diol structure, as well as influence from pH buffer formulation. (See, Springsteen, G.; Wang, B. H. Tetrahedron 2002, 58, 5291; and Yan, J.; Springsteen, G.; Deeter, S.; Wang, B. H. Tetrahedron 2004, 60, 11205.) Boronate ester formation and related mechanisms have also been utilized to develop sensors for carbohydrates and amino acids and selective transporters of nucleosides, saccharides, and nucleotides. (See, e.g., James, T. D.; Sandanayake, K. R. A. S.; Shinkai, S, Nature 1995, 374, 345; James, T. D.; Sandanayake, K. R. A. S.; Shinkai, S. Angewandte Chemie-International Edition 1996, 35, 1910; James, T. D.; Sandanayake, K. R. A. S.; Iguchi, R.; Shinkai, S. Journal of the American Chemical Society 1995, 117, 8982; Mohler, L. K.; Czarnik, A. W. Journal of the American Chemical Society 1993, 115, 7037; Riggs, J. A.; Hossler, K. A.; Smith, B. D.; Karpa, M. J.; Griffin, G.; Duggan, P. J. Tetrahedron Letters 1996, 37, 6303; Mohler, L. K.; Czarnik, A. W. Journal of the American Chemical Society 1993, 115, 2998; and Paugam, M.-F.; Bien, J. T.; Smith, B. D.; Chrisstoffels, L. A. J.; de Jong, F.; Reinhoudt, D. N. Journal of the American Chemical Society 1996, 118, 9820.) It has also been applied in development of medical devices, for example, as part of strategies to construct anti-fouling hydrogel coating and to crosslink polymer hydrogel networks which can go through pH-sensitive sol-gel transition with potential use in targeted drug delivery to GI tract. (See, Winblade, N. D.; Schmokel, H.; Baumann, M.; Hoffman, A. S.; Hubbell, J. A. J. Biomed. Mater. Res. 2002, 59, 618; and Roberts, M. C.; Hanson, M. C.; Massey, A. P.; Karren, E. A.; Kiser, P. F. Adv Mater 2007, 19, 2503).

While boronic acid moieties are common among many therapeutics, effective delivery can be problematic, especially from one compound to another. There remains an ongoing concern in the art to develop a general drug delivery system for targeted therapy of cancer and other disease states, so as to better utilize the benefits and advantages of such boronic acid therapeutics.

SUMMARY OF THE INVENTION

In light of the foregoing, it is an object of the present invention to provide one or more general drug delivery systems and/or methods for their use, by overcoming various deficiencies and shortcomings of the prior art, including those outlined above. It will be understood by those skilled in the art that one or more aspects of this invention can meet certain objectives, while one or more other aspects can meet certain other objectives. Each objective may not apply equally, in all its respects, to every aspect of this invention. As such, the following objects can be viewed in the alternative with respect to any one aspect of this invention.

It can be an object of the present invention to provide a general polymeric system for targeted delivery of a chemotherapeutic compound to enhance permeability and retention effect.

It can be another object of the present invention to provide such a polymeric system with a reversible pH-sensitive boronic acid-diol binding mechanism.

It can be another object of the present invention, alone or in conjunction with one or more of the preceding objectives, to provide such a delivery system with specific cell-surface recognition capability, as can be accomplished through incorporation through a cell-targeting ligand.

Other objects, features, benefits and advantages of the present invention will be apparent from this summary and the following descriptions of certain embodiments, and will be readily apparent to those skilled in the art having knowledge of various chemotherapeutic agents and related delivery systems. Such objects, features, benefits and advantages will be apparent from the above as taken into conjunction with the accompanying examples, data, figures and all reasonable inferences to be drawn therefrom.

In part, the present invention can be directed to a polymeric compound comprising a poly(alkylene oxide) component; a component comprising at least one pendent diol and/or dihydroxyphenyl moiety; and a cell-targeting ligand component, or a salt of such a compound. In certain embodiments, as illustrated below, such a dihydroxyphenyl moiety can be conjugated with a therapeutic agent comprising a boronic acid moiety.

Without limitation, such a compound can comprise a poly(ethylene oxide) component. Regardless, in certain such embodiments, a compound of this invention can comprise a component comprising repeating monomeric units, each of which can comprise a dihydroxyphenyl moiety. In accordance therewith, such a compound can be of a formula

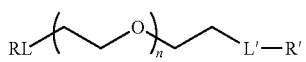

wherein n can be an integer greater than about 30; L' and L can be individually selected from linker moieties; and R' and R can be moieties independently selected from moieties comprising a component of repeating monomeric units, each of which as can comprise a dihydroxyphenyl moiety, moieties comprising a cell-targeting ligand component and combinations thereof.

In certain such embodiments, R can comprise repeating monomeric units. In certain such embodiments, such a compound can be of a formula As illustrated below, such a therapeutic agent can be selected from various anti-cancer therapeutic agents, including but not limited to BTZ. Regardless, a boronic acid moiety of such an agent can be conjugated to a dihydroxyphenyl moiety of a polymeric component of such a compound. As discussed above and illustrated elsewhere herein, such a dihydroxyphenyl moiety can be pendent to a repeating monomeric unit, and such a polymeric component can comprise poly(ethylene oxide). Optionally, such a compound can comprise a cell-targeting ligand component such as but not limited to biotin, representative of various other cancer cell-targeting ligand components. Regardless of identity of therapeutic agent, polymeric component(s), or the presence of a cell-targeting ligand component, such a compound can be incorporated into a pharmaceutical composition comprising a pharmaceutically-acceptable carrier component, as would be understood by those skilled in the art made aware of this invention.

Accordingly, the present invention can also be directed to a method of using a polymeric carrier component to affect efficacy of such a therapeutic agent. Such a method can com-

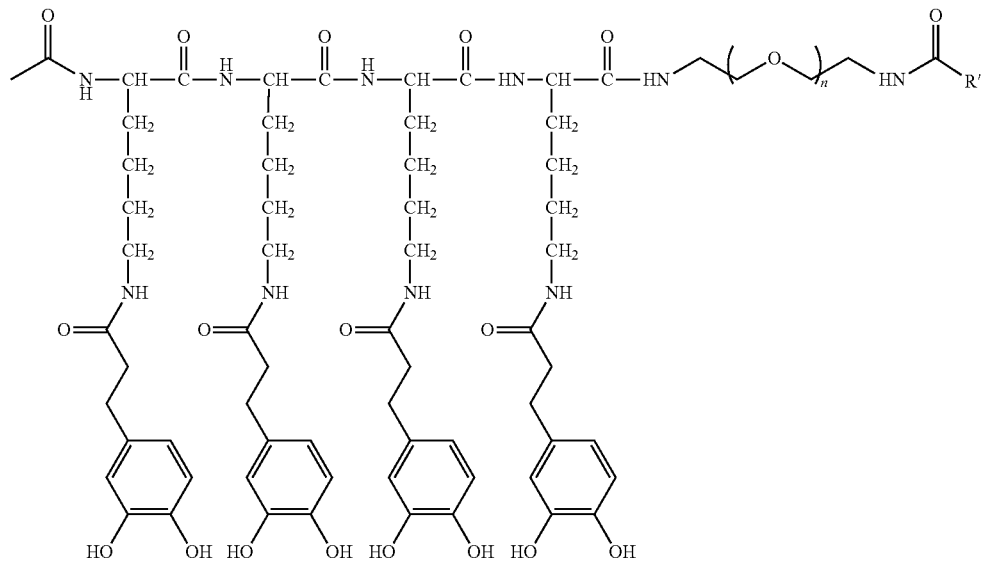

wherein R' can comprise a cancer cell-targeting ligand component. Without limitation, such a ligand component can be biotin. Regardless, with reference to the preceding structural formula, one or more dihydroxyphenyl moieties can be conjugated with a therapeutic agent comprising a boronic acid moiety. In certain such embodiments, such a therapeutic agent can be bortezomib (BTZ), a prodrug of BTZ or a structural analog of BTZ.

In part, the present invention can also be directed to a compound, or a salt thereof, comprising a polymeric component comprising a component comprising at least one pendent diol moiety, such a polymeric component as can be conjugated with a therapeutic agent, such conjugation via such a diol moiety and a boronic acid moiety of such a therapeutic agent. In certain embodiments, such a polymeric component can comprise a poly(alkylene oxide), including but not limited to poly(ethylene oxide). In certain such or other embodiments, such a compound can comprise a cell-targeting ligand component and/or a dihydroxyphenyl moiety, the latter as can be bound, coupled or otherwise pendent to a repeating monomeric unit.

prise providing a therapeutic agent comprising a boronic acid moiety; conjugating such a polymeric carrier component with a therapeutic agent, such conjugation as can be by a reversible pH-sensitive bond between a diol moiety of such a carrier compound and such a boronic acid moiety of a therapeutic agent; and introducing and/or administering such a conjugated compound to a cellular environment comprising a pH at least sufficient to dissociate such a therapeutic agent from such a conjugated compound.

In part, the present invention can also be directed to a method for affecting and/or inhibiting a cancer proteasome. Such a method can comprise contacting, in vivo or in vitro, a human cancer cell expressing a protease with an effective amount of a compound comprising a poly(alkylene oxide) component, a component comprising at least one pendent catecholic component, and a cell-targeting ligand component, such a catecholic component as can be conjugated with a bortezomib component, such conjugation as can be via the dihydroxyphenyl moiety of such a catecholic component and the boronic acid moiety of such a bortezomib component. In certain such embodiments, such a compound can comprise a poly(ethylene oxide) component. Regardless, such a catecholic component can be pendent to a repeating monomeric component. Any such compound(s) can be provided as part of a pharmaceutical composition comprising a pharmaceutically-acceptable carrier component for use in conjunction with such a method.

Regardless, in certain embodiments of the present method(s), such a therapeutic agent can be selected from BTZ, a pro-drug of BTZ and a structural analog of BTZ. Regardless, dissociation of such a conjugated compound can be extracellular and/or intracellular, such dissociation as can be effected at a pH less than about 7.4. In certain such or other embodiments, such a polymeric carrier component can comprise a poly(ethylene oxide) component of molecular weight at least partially sufficient to affect degradation of such a conjugated compound. In accordance therewith, such a poly(ethylene oxide) component can comprise about 30-about 250 repeating monomeric units or, alternatively, up to about 2,500 or more repeating monomeric units. In certain such embodiments, without limitation, such a compound or a salt thereof can comprise a plurality of pendent dihydroxyphenyl moieties (e.g., without limitation, up to about 4, or about 8 or more) to enhance loading and delivery of such a therapeutic agent.

Optionally, such a polymeric carrier component can comprise a cell-targeting ligand component. For introduction/administration to a cellular environment and/or medium comprising a mass and/or tumor of cancer cells, a ligand component such as but not limited to biotin can be employed. In certain such embodiments, as demonstrated below, such a conjugated compound can comprise a polymeric carrier component comprising a poly(ethylene oxide) component and a therapeutic agent as can be, for instance, selected from BTZ, a pro-drug of BTZ and a structural analog of BTZ.

DETAILED DESCRIPTION OF THE DRAWINGS

FIG. 1. In accordance with certain non-limiting embodiments of this invention, a schematic illustration of biocompatible polymers presenting a catechol group that can associate with boronic acid-containing drugs in a reversible and pH-sensitive manner.

FIGS. 2A-B. (A) pH-sensitive polymer-drug conjugates for delivering bortezomib selectively into cancer cells. Catechol polymer-bortezomib conjugate dissociates in response to decreased pH in cancer microenvironment and intracellularly in the endosome, releasing free, active drug to cancer cells. (B) At physiologically neutral pH, catechol and the boronic acid structure in bortezomib form a stable covalent conjugate. Such conjugate dissociates as the environment becomes acidic.

Figure 3A:
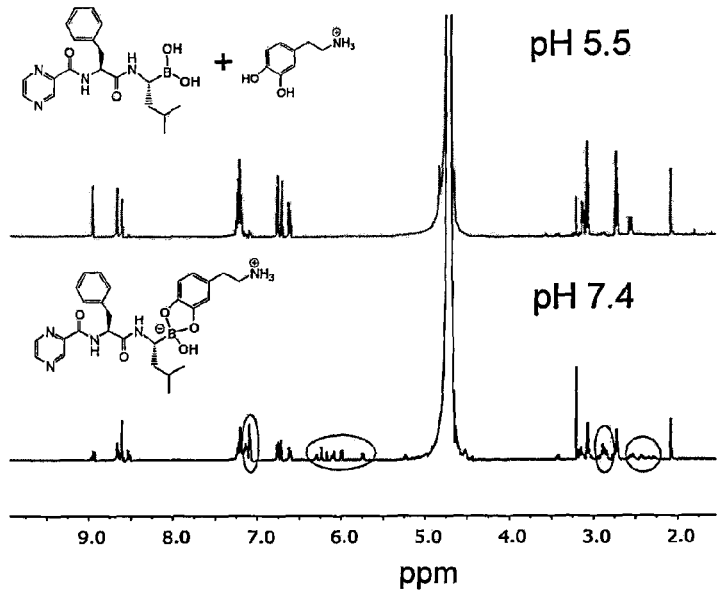
Figure 3B:
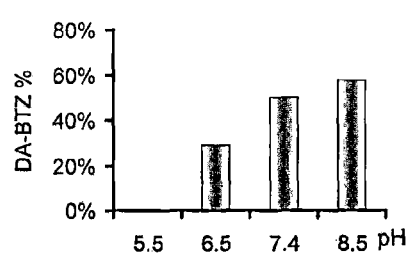
Figure 3C:
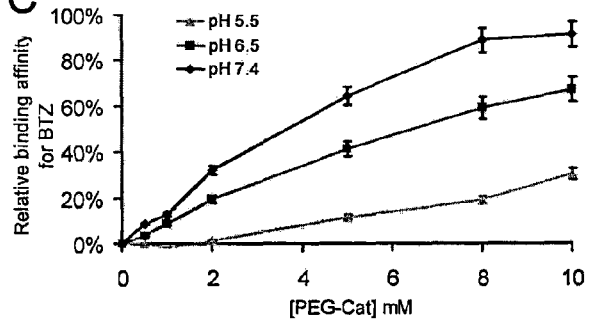

FIGS. 3A-C. pH-dependent interactions between bortezomib and catechol. (A) H1-NMR spectra of BTZ and dopamine (DA) in deuterated PBS at pH 5.5 and 7.4. Dopamine was chosen as a representative catechol-containing model compound whose conjugate with BTZ is fully soluble in aqueous solutions. Circled in red are proton signals resulting from the formation of a stable dopamine-BTZ conjugate at pH 7.4, which are not present at pH 5.5. (B) Peak integrals in the ranges of 7.0~7.2, 6.6~6.8 and 5.5~6.5 ppm were used to estimate the degree of BTZ-DA binding at pH 5.5 to 8.5. (C) Characterization of the pH dependence of BTZ-catechol binding by 3-component fluorescence assay. PEG-Cat (Scheme 1) was used as a model catechol-containing polymer to reveal catechol binding affinity for BTZ at pH 5.5, 6.5 and 7.4.

Figure 3D:
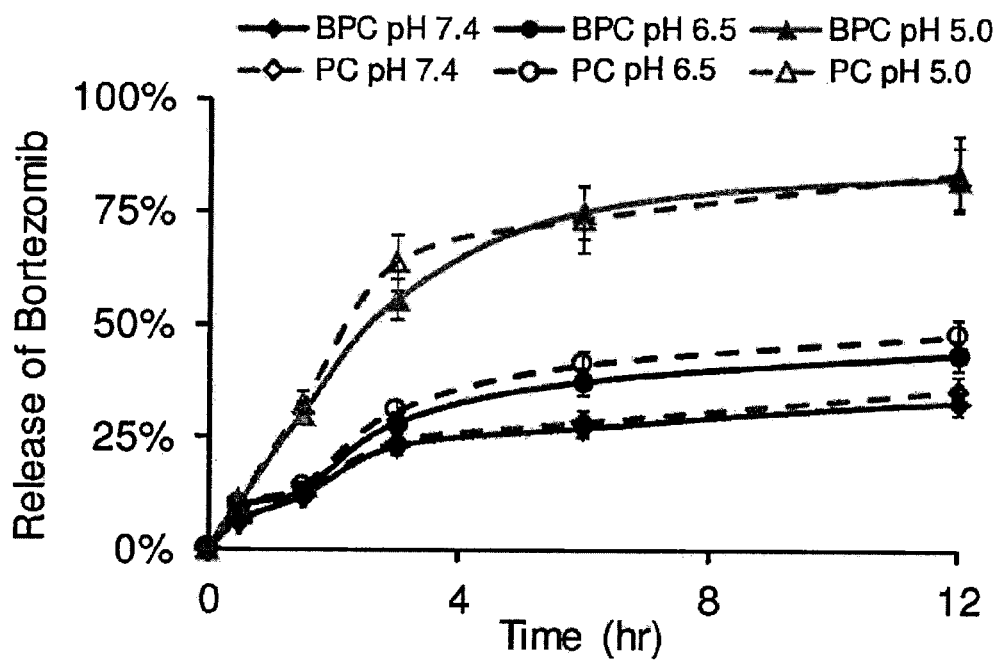

FIG. 3D. Time-dependent release of BTZ from the catechol polymers BPC and PC at pH 5.0, 6.5, and 7.4. The fraction of BTZ released was 30% from both polymers at pH 7.4 over 12 h, while 80% of the BTZ was released at pH 5.0 in the same period of time. Drug-polymer conjugates formed between 0.2 mM and 0.05 mM BPC or PC were used for all measurements of release in 10 mM PBS buffers at 37° C.

Figure 4:
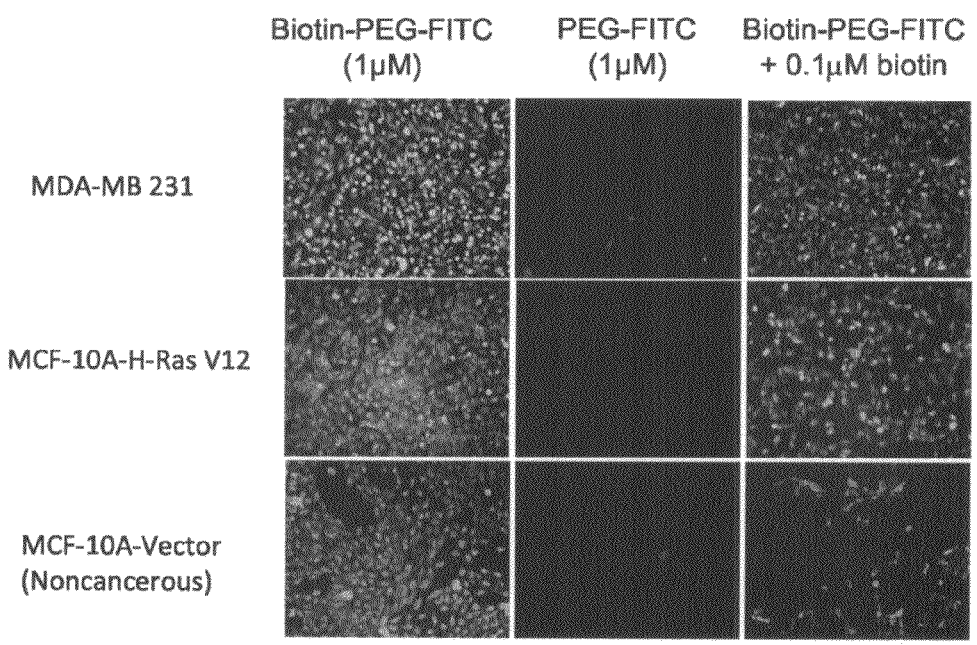

FIG. 4. Selective uptake of fluorescent FITC-terminated PEG molecules by cancer cells (MDA-MB231 and MCF-10A-H-RasV12) and noncancerous cells (MCF-10A vector). All cells treated with 1 µM biotin-PEG-FITC showed uptake of biotin-PEG-FITC but little of PEG-FITC. Free biotin (0.1 µM) in culture media most effectively inhibited uptake of biotin-PEG-FITC by noncancerous cells but not 2 cancerous cells, indicating the entry of FITC-terminated polymers is mediated by biotin receptors on cell surface and expression of such receptors on cancer cell surface is very likely higher than on noncancerous cell surface. All images were taken after 15 minute-treatment using an inverted fluorescent microscope at 10× magnification.

FIGS. 5A-C. Cytotoxicity of catechol-presenting polymer-BTZ conjugates against breast cancer cells. (A) Proteasome inhibition assays at 6 hours post treatment of MDA-MB 231 cells with free BTZ (I), BPC-BTZ (II), PC-BTZ (III). IV and V represent BPC and PC without BTZ. (B) Cell viability was determined by fluorescence imaging at 48 hours post treatment using a commercial cell viability assay kit (calcein AM for live cells and ethidium homodimer-1 for dead cells). (C) $IC_{50}$ values of BPC-BTZ estimated from cell proliferation MTS assays indicate the selective toxicity of BPC-BTZ toward cancer cells over noncancer cells.

Figure 6:
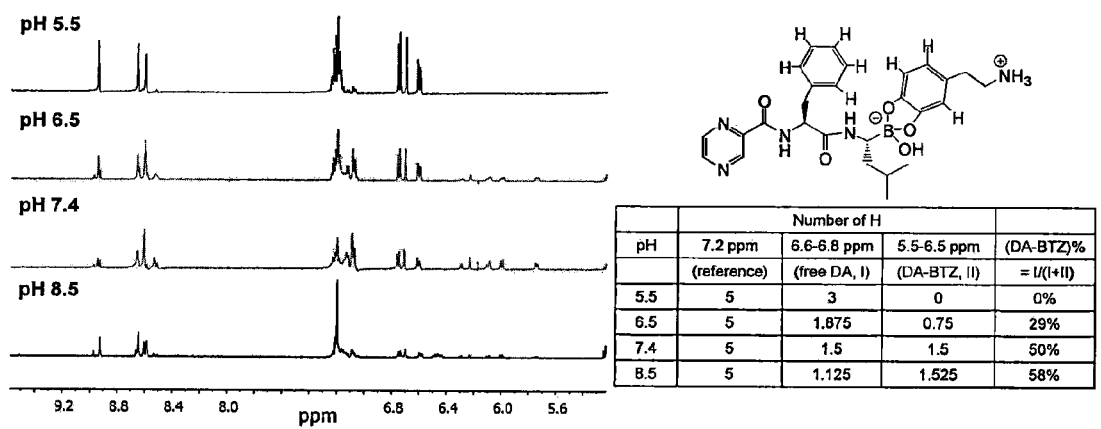

FIG. 6. Characterization of pH-dependent association of the dopamine-bortezomib conjugate (DA-BTZ) by $H^1$-NMR. The peaks around 7.2 ppm correspond to H atoms on the phenyl ring of bortezomib (highlighted in blue). The peaks between 6.6 and 6.8 ppm represent Hs on the catechol ring of DA (highlighted in red). In DA-BTZ conjugates, Hs on the catechol ring shifted to the range of 6.5~5.5 ppm. Peak integrals from the ranges above were used for calculating degree of DA-BTZ association.

FIG. 7A-B. (A) Standard ARS-bortezomib binding curves at pH 5.0~8.0 shows little dependency on pH. Therefore, ARS-bortezomib complex can be used to study pH-dependent affinity of a competing diol (e.g. catechol) for bortezomib by measuring dose-dependent fluorescence change. (B) Inhibition of fluorescence from ARS-bortezomib binding upon addition of the catechol-containing compound PEG-Cat at different pH.

FIGS. 8A-D. Cryo-TEM analysis was performed on Hitachi H-8100 transmission electron microscope using solutions containing 0.25 mM BPC in 0.1 M phosphate monosodium buffer before (A and B) and after (C and D) conjugation of 1 mM bortezomib at pH 7.4. The scale bars are 0.2 µM in A and C and 0.1 µM in B and D.

Figure 9:
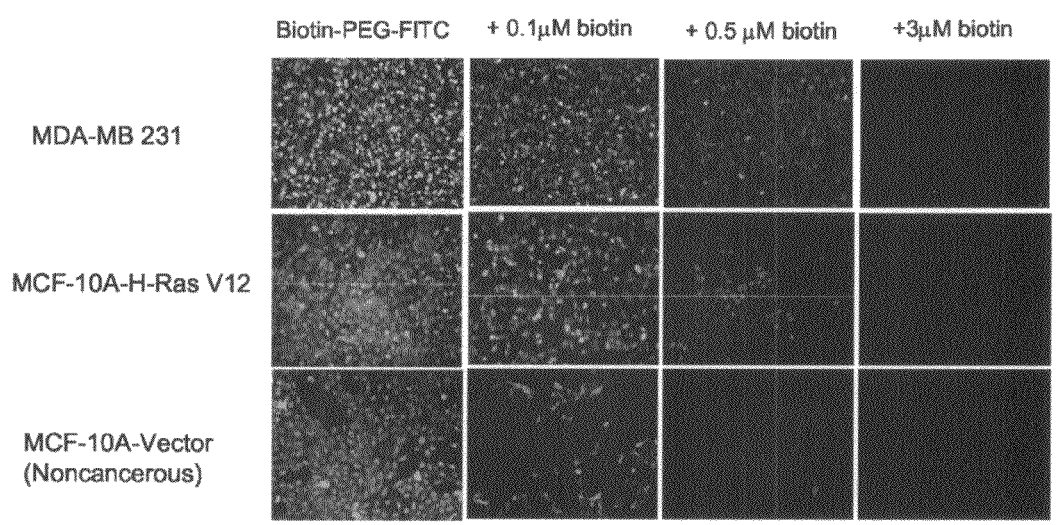

FIG. 9. Dose-dependent inhibition of cellular uptake of biotin-PEG-FITC by free biotin. Although cancerous and noncancerous cells were able to take up the biotinylated fluorescent polymer, higher concentrations of free biotin were needed to inhibit polymer uptake by cancer cells compared to noncancerous cells, implying higher expressions of biotin receptor on cancer cell surface. All images were taken after 15 minute-treatment.

Figure 10:
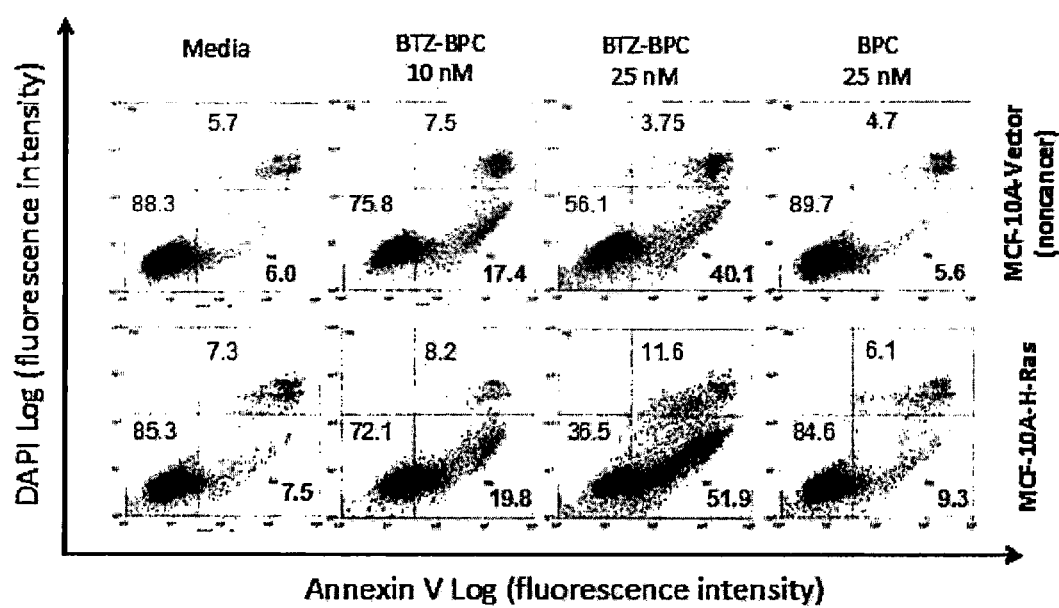

FIG. 10. Cell death induced by BPC-BTZ conjugate was measured using flowcytometry with Annexin-V/DAPI staining. In each panel, the lower-left (Annexin-V$^-$, DAPI$^-$), lower-right (Annexin-V$^+$, DAPI$^-$), and upper-right (Annexin-V$^+$, DAPI$^+$) quadrants represent the populations of live cells, apoptotic cells, and necrotic/dead cells, respectively. The average % population in each quadrant is indicated by the numbers at the corners of the panels. These data show that non-cancerous MCF-10A breast epithelial cells stably expressing empty vector (i.e., control cells) were less sensitive than MCF-10A cells stably transformed with the H-RasV12 oncogene (i.e., cancerous cells) to BPC-BTZ-induced cell apoptosis and necrosis.

Figure 11:
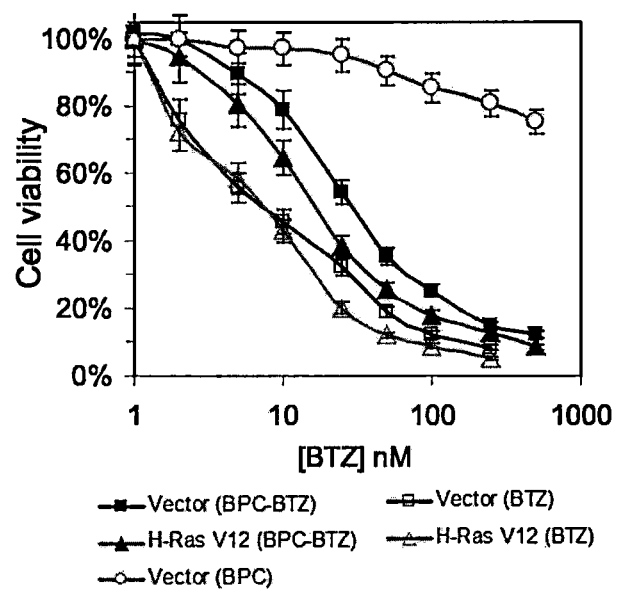

FIG. 11. Dose-dependent cytotoxicity of BPC-BTZ, free BTZ, or polymer only (BPC) against MCF-10A-vector and MCF-10A-H-RasV12 cells. SigmaPlot software was used for sigmoidal logistic fitting to obtain $IC_{50}$ values shown in FIG. 5C.

DETAILED DESCRIPTION OF CERTAIN EMBODIMENTS

Certain embodiments of this invention can be described in terms of a reversible, pH-sensitive boronic acid-diol binding mechanism to provide a new drug delivery system for targeted therapy of cancer and other disease states, utilizing boronic acid-containing therapeutics without unwanted systematic toxicity. Such drug delivery systems can comprise biocompatible polymers presenting a tissue-targeting ligand to direct drug distribution to diseased tissue, a polyethylene oxide) moiety to increase blood circulation time, and a diol structure, e.g., 1,2-benzenediol (catechol), for association with a boronic acid structure in therapeutics of interest. (FIG. 1) Chemoselective binding between catechol and boronic acid moieties at a physiological and/or basic pH presents such a conjugate as an inactive pro-drug that has dramatically reduced cell permeability and subsequently decreased systematic toxicity to healthy tissues.

More specifically, as relates to certain non-limiting embodiments, a polymer conjugate of the anticancer drug bortezomib (BTZ) can be utilized for pH-sensitive delivery to specific cancer cells. BTZ is a dipeptide boronic acid analogue that inhibits cancer cell proteasome through direct binding between its boronic acid group and threonine residues in the active sites of several proteases. (See, Adams, J.; Behnke, M.; Chen, S.; Cruickshank, A. A.; Dick, L. R.; Grenier, L.; Klunder, J. M.; Ma, Y.-T.; Plamondon, L.; Stein, R. L. Bioorg Med Chem Lett 1998, 8, 333-338 and Groll, M.; Berkers, C. R. Ploegh, H. L.; Ovaa, H. Structure 2006, 14, 451-456.) Currently, this drug is approved for multiple myeloma treatment; however, its use in treating other cancers especially solid tumors has been shown to be much less efficient and often requires high doses with significant systematic toxicity. In addition to the possibility that different cancer cells may have distinct proteasome sensitivity to BTZ, the unfavorable pharmacokinetic properties of BTZ including nonspecific binding to proteins and rapid hepatic clearance from blood may also contribute to its limited use in treatment of solid tumors. Such deficiencies suggest a possible benefit to use of polymer delivery vehicles capable of enhancing circulation time of BTZ. Moreover, co-strategies for directing BTZ to cancer cells by specific cell recognition and/or acidity-targeting may enable the drug to concentrate in target cancer tissues, and therefore increase the anti-cancer effects while minimizing peripheral toxicity to healthy cells.

Figure 2:
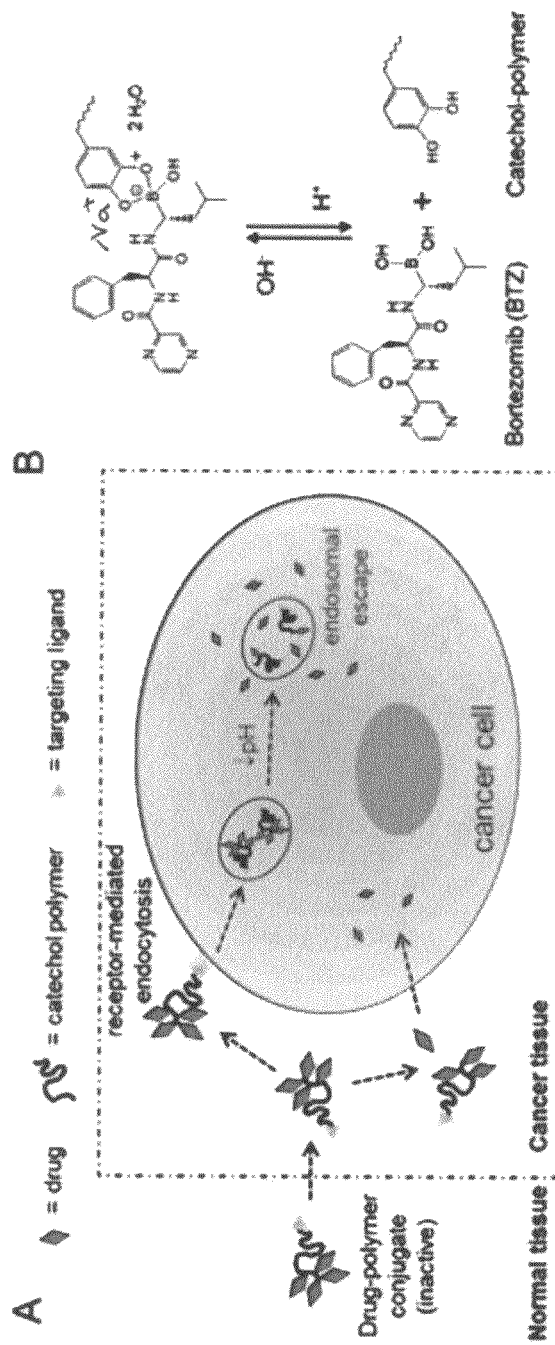

It has been previously reported that the binding of BTZ and polyphenols can chemically block the proteasome inhibiting activity of BTZ because the formed conjugates were not freely permeable through cell membrane. However, in contrast to the prior art, this invention takes advantage of the facile conjugation of BTZ to a 1,2-benzenediol (e.g., catechol) moiety to form a membrane-impermeable compound in order to reduce nonselective cellular uptake of the drug. A pertinent characteristic of such a boronic acid-catechol conjugate is that the covalent chemistry is reversible in a pH-sensitive manner: at beyond neutral pH, BTZ and catechol form a stable ester of boronic acid (e.g., the sodium or an alkali-metal salt thereof), which deactivates the cytotoxicity of BTZ; in low pH environment, the BTZ-catechol ester conjugate readily dissociates to release free BTZ from the catechol groups. This mechanism can be exploited for localized drug release extracellularly at tumor tissue typically with a mild pH decrease, as well as intracellularly in the more acidic endosomes following cell surface recognition-mediated endocytosis. In either case, the acidic environment induces BTZ dissociation from the catechol groups as a free drug to inhibit proteosome function (FIG. 2).

First, the pH-dependent reversible binding between BTZ and catechol-containing polymers was characterized using $H^1$-NMR spectroscopy (FIG. 3A). At pH 5.5, mixing BTZ and catechol-containing dopamine (DA) gave a spectrum similar to that of the two individual compounds superimposed on each other, indicating the presence of un-complexed BTZ and DA. However, the same mixture at pH 7.4 gave a spectrum with obvious changes in chemical shifts and splitting of peaks, revealing formation of a BTZ-catechol conjugate. (To further look at the pH-sensitivity of BTZ-catechol dissociation, pre-formed BTZ-catechol conjugate (0.1 M in deuterated DMSO) was diluted to 1 mM in deuterated phosphate buffers at pH from 5.5 to 8.5, and then analyzed by NMR (See, example 7 and FIG. 6). The peak integrals in the ranges of 7.2~7.0, 6.6~6.8, and 5.5~6.5 ppm, corresponding separately to the H atoms on the phenyl ring of BTZ, those on the benzene ring of free DA, and the benzene H shifted due to BTZ-DA formation, were used to estimate the degree of BTZ-catechol conjugation). As shown in FIG. 3B, dissociation of the BTZ-catechol conjugate increased 50% as the pH decreased from 7.4 to 5.5. (Alternatively, the pH-sensitive BTZ-catechol binding was verified by a fluorescence assay described in the literature (see, example 8 and FIG. 7). (See, Springsteen, G.; Wang, B. H. Tetrahedron 2002, 58, 5291-5300.) Related data shows that the binding affinity of a catechol-presenting polymer PEG-Cat (Scheme 1) for BTZ decreased about 60% from pH 7.4 to pH 5.5 (FIG. 3C).

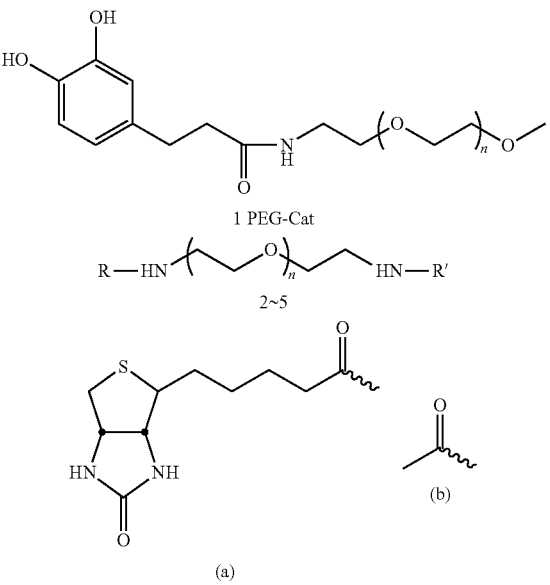

Scheme 1.

-continued

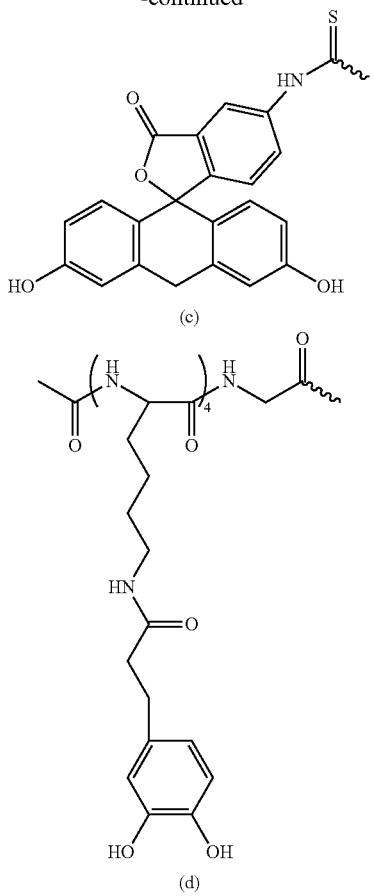

2 Biotin-PEG-FITC
3 PEG-FITC
4 BPC
5 PC

R = a, R' = c
R = b, R' = c
R = a, R' = d
R = b, R' = d

The pH dependence of the BTZ-catechol association and dissociation suggested that polymer constructs containing catechol moieties would be useful for acidity-triggered release of BTZ. To synthesize several BTZ-polymer constructs as acidity-responsive carriers of BTZ to cancer cells (Scheme 1), a modular design was employed consisting of one or more catechols moieties pendent to a poly(ethylene oxide) or poly(ethylene glycol) (PEG) polymer with a cell targeting moiety. PEG is well-known to reduce nonspecific interactions with proteins and cells, and therefore has been widely applied in the form of drug-PEG conjugates that exhibit reduced drug degradation and extended drug circulation time. (See, Veronese, F. M.; Pasut, G. Drug Discov Today 2005, 10, 1451-1458.) Biotin was used as a representative cell-targeting ligand because it has been previously reported that biotinylated polymers can be selectively taken up by cancer cells. Although expression of biotin receptors/transporters on cancer cell surfaces has not been well characterized, biotin has a relatively simple structure and can be used as a tag simultaneously for cellular tracking of our polymer drug carriers, making this molecule an attractive choice for cancer-targeting.

Fluorescence microscopy was used to examine the uptake of fluorophore-labeled biotinylated PEG (biotin-PEG-FITC) into 2 breast cancer cell lines, MDA-MB-231 and MCF-10A-H-RasV12, as well as a normal breast epithelial cell line MCF-10A-Vector. FIG. 4 shows that biotin-PEG-FITC was rapidly taken up by cells, whereas the cellular uptake of PEG-FITC without the biotin moiety was minimal. The uptake of biotinylated polymers was inhibited by free biotin in a dose-dependent manner (see, example 10 and FIGS. 8A-D and 9), demonstrating that polymer uptake by cells is mediated by the cell surface receptor for biotin. (The uptake of biotinylated polymer by cancer cell lines (MDA-MB-231 and MCF-10A-H-RasV12) was less inhibited by free biotin than that by noncancer MCF-10A-Vector cells, implying a higher expression of biotin receptors on cancer cell surfaces).

With confirmation of the cancer-targeting function of the biotin ligand, PEG polymers were synthesized to provide 4 catechol groups for conjugating BTZ, allowing multiple drug molecules to be loaded onto the polymeric carrier. Reference is made to Scheme 1, BPC and PC, above; and FIG. 3C.) Time-dependent release of BTZ from these catechol polymers was carried out in buffered solutions at pH 7.4, 6.5, and 5.0, mimicking the physiological pH in normal tissue and blood, the tumor extracellular environment, and subcellular endosome, respectively. FIG. 3D shows that at pH 7.4, ~30% of the BTZ was released from both BPC and PC over a 12 h period, while >80% of the BTZ was released from these catechol polymers at pH 5.0. This further confirmed the pH-dependent BTZ dissociation from the catechol-presenting polymeric delivery vehicles, which could render BTZ non-cell-permeable and inactive in normal tissues but allow the BTZ activity to be recovered in cancer tissue, where the acidity increases.

The effects of polymer-BTZ conjugates on proteasome inhibition and cell viability were first evaluated using MDA-MB-231 cells (FIGS. 5A-B). Untargeted (without the biotin ligand) PC-BTZ conjugate has dramatically decreased proteasome inhibition in comparison to free BTZ, indicating the deactivation of BTZ due to formation of BTZ-catechol-polymer conjugate that is unable to diffuse readily into the cells, consistent with previously reported inhibition of BTZ by polyphenols. To the contrary, the biotinylated, cancer-cell targeting BPC-BTZ conjugate retained high proteasome-inhibiting activity. Without limitation to any one theory or mode of operation, these results suggest that cellular uptake of polymer-BTZ conjugate through biotin-receptor mediated transportation could restore BTZ activity within the cells, perhaps via internalization of the polymer-BTZ conjugate followed by the dissociation of BTZ from the polymer intracelluarly. Cell viability assays at 48 hours post treatment of cells with the polymer-BTZ conjugates demonstrated a similar pattern: the biotin-receptor targeting BPC-BTZ conjugate maintained fairly high cytotoxicity of BTZ.

To further evaluate the selectivity of the polymer-drug conjugates for cancer cells over normal cells, immortalized human mammary epithelial cells MCF-10A vector (non-cancer control) and transformed MCF-10A-H-RasV12 cancerous cells were treated with BPC-BTZ (0, 10, 25 nM). It was found that BPC loaded with BTZ at 25 nM concentration induced 1.7-fold increased cell death in the cancerous cell compared to the control cells (see, example 14 and FIG. 10.) Calculated $IC_{50}$ values for cell growth inhibition by BPC-BTZ and free BTZ also showed 2.2-fold increase in selective toxicity on cancerous cells over control cells (FIG. 5C). Such result demonstrated that cancer cells are more susceptible to BPC-BTZ toxicity than noncancer cells.

Methods and compounds of the present invention can also, as would be understood by those skilled in the art, be extended to include such compounds or methods in conjunction with a pharmaceutical composition comprising a compound of the sort described herein and a physiologically or otherwise suitable formulation. In a some embodiments, the present invention includes one or more of the present compounds, as set forth above, formulated into compositions together with one or more physiologically tolerable or acceptable diluents, carriers, adjuvants or vehicles that are collectively referred to herein as carriers. Compositions suitable for such contact or administration can comprise physiologically acceptable sterile aqueous or nonaqueous solutions, dispersions, suspensions or emulsions. The resulting compositions can be, in conjunction with the various methods described herein, for administration or contact with a human/animal cancer cell and/or a protease expressed or otherwise present therein. Whether or not in conjunction with a pharmaceutical composition, "contacting" means that a cancer cell and one or more of the present compounds are brought together for purpose of binding and/or complexing such a compound to a proteosome and/or protease. Amounts of a compound effective to inhibit a protease may be determined empirically, and making such determinations is within the skill in the art. Inhibition or otherwise affecting protease activity includes both reduction and/or mitigation, as well as elimination of protease activity.

It is understood by those skilled in the art that dosage amount will vary with the activity of a particular compound, disease state, route of administration, duration of treatment, and like factors well-known in the medical and pharmaceutical arts. In general, a suitable dose will be an amount which is the lowest dose effective to produce a therapeutic or prophylactic effect. If desired, an effective dose of such a compound, pharmaceutically-acceptable salt thereof, or related composition may be administered in two or more sub-doses, administered separately over an appropriate period of time.

Methods of preparing pharmaceutical formulations or compositions include the step of bringing an inhibitor compound into association with a carrier and, optionally, one or more additional adjuvants or ingredients. For example, standard pharmaceutical formulation techniques can be employed, such as those described in Remington's Pharmaceutical Sciences, Mack Publishing Company, Easton, Pa.

Regardless of composition or formulation, those skilled in the art will recognize various avenues for administration, together with corresponding factors and parameters to be considered in rendering such a medicament suitable for administration. Accordingly, with respect to one or more non-limiting embodiments, the present invention provides for use of one or more compounds for the manufacture of a composition for therapeutic use in the treatment of a human cancer.

The compounds of the present invention can suitably comprise, consist of or consist essentially of any of the aforementioned components and/or moieties thereof. Each such compound, or component or moiety thereof, can be compositionally distinguishable, characteristically contrasted and can be practiced in conjunction with the present invention, separate and apart from another. Accordingly, it should also be understood that the inventive compounds, compositions and/or methods, as illustratively disclosed herein, can be practiced or utilized in the absence of any one compound, component and/or moiety which may or may not be disclosed, referenced or inferred herein, the absence of which may or may not be specifically disclosed, referenced or inferred herein—such practice and/or utilization as can be hereafter claimed and supported herewith, and as can patentably distinguish certain embodiments of this invention.

EXAMPLES OF THE INVENTION

The following non-limiting examples and data illustrate various aspects and features relating to the compounds, compositions and/or methods of the present invention, including the preparation of various polymer-drug conjugates, as are available through the synthetic methodologies described herein. In comparison with the prior art, the present compounds, compositions and/or methods provide results and data which are surprising, unexpected and contrary thereto. While the utility of this invention is illustrated through the use of several compounds/compositions, ligand components, polymer components and/or moieties thereof and therapeutic agents that can be used therewith, it will be understood by those skilled in the art that comparable results are obtainable with various other compounds/compositions, ligand components, polymer components/moieties and therapeutic agents, as are commensurate with the scope of this invention Materials and General Procedures:

$CH_3O$-PEG-$NH_2$ (average MW 500) and mono-protected di-amine terminated PEG (average MW 2000) were purchased from LaysanBio, INC (Arab, Ala.). Fmoc protected amino acids, synthesis resins and d-biotin were purchased from Anaspec, Inc. (Fremont, Calif.). Bortezomib was purchased from ChemieTek (Indianapolis, Ind.). All other chemicals, unless stated otherwise, were purchased from Sigma-Aldrich. Nuclear magnetic resonance (NMR) spectra were recorded on AVANCE III 500 MHz with direct cryoprobe. Spectra were recorded in $CDCl_3$ or $D_2O$ solutions at 293K. LC-MS analysis was performed on an Agilent 6520 quadrupole time-of-flight (Q-TOF) mass spectrometer. MALDI-TOF MS analysis was performed in positive mode on Bruker Apex III MALDI TOF mass spectrometer.

Example 1

Synthesis of PEG-Catechol (Compound 1)

100 mg (0.2 mmol) of $CH_3O$-PEG-$NH_2$ (average MW: 528) was dissolved in 4 ml DMF, to which a solution of 72 mg (0.4 mmol) 3-(3,4-dihydroxyphenyl)propionic acid (DHPA), 177 mg (0.4 mmol) BOP, 54 mg (0.4 mmol) HOBT and 350 μl DIPEA in 1 ml DMF was added dropwise. The mixture was stirred at room temperature for 8 hours. Completion of the amide formation between $PEG_{550}$-$NH_2$ and DHPA was confirmed by a negative ninhydrin test. 30 ml cold ether was added to precipitate the crude product, centrifuged at 0° C. to remove supernatant and an oil-to-wax-like residue was obtained. 5 ml DIUF $H_2O$ was added to dissolve the residue and the solution was filtered through 0.45 μm pore size membrane filter. Lyophilization of the filtrate gave the product as a pale-yellow wax.

$^1$H NMR ($CDCl_3$, 500 MHz) δ (ppm): 6.5~6.7 (m, 3H), 3.50~3.70 (bm, 56H), 2.81 (dd, 2H), 2.68 (dd, 2H).

MS $(M+1)^+$: average MW 692.6.

Example 2

Synthesis of Biotin-PEG-$NH_2$ 0.1 mmol (200 mg) of tBoc-NH-PEG-$NH_2$ (average MW 1990.2) was dissolved in 500 μl DMF and 0.2 mmol (42 mg) biotin was dissolved separately in 500 μl DMSO. The two solutions were mixed and 0.2 mmol BOP, 0.2 mmol HOBT and 0.25 mmol DIPEA in 500 μl DMF were added. The reaction mixture was stirred at room temperature for 12 hours. A negative ninhydrin test confirmed completion of the amide formation between (tBoc)NH-PEG-$NH_2$ and biotin. 30 ml cold ether was added to precipitate the crude product, centrifuged at 0° C. to remove the supernatant and a waxy residue was obtained. Without further purification, deprotection of tBoc group on the crude product was carried out as follows. About 220 mg crude product (tBoc)NH-PEG-NH-biotin was dissolved in a mixture of 5 ml DCM and 5 ml TFA. The solution was stirred at room temperature for 2 hours and the solvent was evaporated under vacuum. 2 ml TFA was added to dissolve the oily residue and 30 ml cold ether was added to precipitate the crude product. Centrifugation of the mixture at 0° C. gave a soft wax-like product. 5 ml DIUF $H_2O$ was added to dissolve the residue and the solution was filtrated through a 0.45 μm pore size membrane filter. Lyophilization of the filtrate gave the product biotin-PEG-$NH_2$.TFA as a white, solid wax.

MS $(M+1)^+$: average MW 2117.0

Example 3

Synthesis of Biotin-PEG-FITC (Compound 2)

50 mg (0.024 mmol) TFA salt of biotin-PEG-$NH_2$ was dissolved in 1 ml DMF and neutralized with 100 μl DIPEA.

A solution of 15 mg (0.039 mmol) fluorescein 5-isothiocyanate in 500 μl DMF was added and the mixture was stirred for 4 hours at room temperature. The mixture was diluted in 20 ml DMF and extracted with 5 ml 0.1 N HCl in $H_2O$, 5 ml $H_2O$ and 5 ml saturated NaCl in $H_2O$. The DMF solution was dried over $MgSO_4$ and evaporation of the solvent under vacuum gave the product as a yellow oil. (39 mg, yield 80%).

MALDI-TOF MS $(M+Na)^+$: average 2504.1

Example 4

Synthesis of Fully Protected Peptide Ac-[Lys(tBoc)]$_4$-Gly-OH

Standard solid phase peptide synthesis was carried out using Fmoc protected amino acids with BOP/HOBT as coupling agents. Briefly, 200 mg glycine-loaded 2-chlorotrityl resin (0.8 meq/g) was washed and swelled in DMF. 225 mg (0.48 mmol, 3 eqv.) Fmoc-Lys(tBoc)-OH, 212 mg (0.48 mmol) BOP, 65 mg (0.48 mmol) HOBT and 90 ul DIPEA were dissolved in 4 ml DMF and added to the resin. The reaction vessel was vigorously rocked for 4 hours and negative ninhydrin test indicated the coupling was complete. The resin was washed with DMF 3 times and a solution of 20% piperidine in DMF was used to remove the Fmoc group and expose the free amine groups on the peptide-conjugated resin for the next coupling cycle. Such coupling and deprotection cycle was repeated 4 times. After exposure of amine groups on [Lys(tBoc)]$_4$-Gly-resin, a solution of 1 ml acetyl anhydride and 300 μl DIPEA in 4 ml DMF was used to cap the α-amine of the last lysine residue. The resin was washed thoroughly in DMF and then DCM prior to drying under vacuum overnight. The dried resin was suspended in 10 ml of a DCM solution containing 1% TFA and gently stirred at room temperature for 1 hour. The suspension was filtered through a glass filter to remove the resin, and the filtrate was concentrated to about 1 ml under vacuum. Cold $H_2O$ was added to precipitate the product peptide acid and suction filtration gave the product as a white solid powder. Without further purification, this crude product was directly used to synthesize Ac-(Lys)$_4$-Gly-PEG-biotin.

MALDI-TOF MS $(M+Na)^+$: 1052.7, $(M-1)^-$: 1028.5

Example 5

Synthesis of Ac-(Lys)$_4$-Gly-PEG-Biotin 110 mg (~0.05 mmol) compound 2 was dissolved in 2 ml DMF and neutralized with 100 μl DIPEA. 42 mg (~0.04 mmol) Ac-[Lys(tBoc)]$_4$-Gly-OH, 22 mg (0.05 mmol) BOP, 7 mg (0.05 mmol) HOBT and 25 μl IPEA was mixed in 1 ml DMF and the mixture was added to the neutralized solution of compound 2. The final reaction mixture was stirred at room temperature for 16 hours. 20 ml diethyl ether was added to precipitate the crude product and centrifugation of the mixture at 0° C. gave a waxy residue. 10 ml of a solution containing 50% DCM and 50% TFA was used to dissolve the residue and stirred at RT for 3 hours to remove the tBoc groups at the side chains of lysine on the PEG-peptide conjugate. The reaction mixture was concentrated under vacuum to about 2 ml and 25 ml cold ether was added. After centrifugation of the mixture at 0° C., crude product was obtained. 10 ml DIUF $H_2O$ was added to dissolve the residue and lyophilization of the solution gave the product compound 4 as white, solid wax/powder, which was further purified by RP-HPLC.

MALDI-TOF MS $(M+1)^+$: average 2728.4

Example 6

Synthesis of Ac-[Lys(ε-NH-catechol)]$_4$-Gly-PEG-biotin (BPC)

50 mg (~0.018 mmol) Ac-(Lys)$_4$-Gly-PEG-biotin was dissolved in 1 ml DMF and neutralized with 50 μl DIPEA. 37 mg (0.2 mmol) DHPA, 0.2 mmol DBTU, 0.2 mmol HOBT and 130 μl DIPEA were mixed in 2 ml DMF and the mixture was added to the neutralized solution of Ac-(Lys)$_4$-Gly-PEG-biotin. The final reaction mixture was stirred at room temperature for 20 hours. 25 ml diethyl ether was added and centrifugation of the mixture at 0° C. gave a light brown, waxy residue. This crude product was further purified by RP-HPLC.

MALDI-TOF MS $(M+Na)^+$: average 3406.7

Example 7

$H^1$-NMR Analysis of pH-Dependent Dissociation of Bortezomib-Catechol Conjugates Bortezomib and dopamine hydrogen chloride were dissolved separately in $d_6$-DMSO 0.2 M concentration. The two solutions were mixed to give a stock solution of DA-BTZ conjugate at 0.1 M in DMSO. A solution of 0.1 M monosodium phosphate in $D_2O$ was used to dilute the DA-BTZ stock to 1 mM, and pH of such solutions were adjusted with 4N NaOH in $D_2O$ to 5.5, 6.5, 7.4 and 8.5. These solutions were analyzed on AVANCE III 500 MHz (FIG. 6) and peak integrals in the range of 7.2 to 5.5 ppm were used for quantifying the degree of dissociation of DA-BTZ presented in FIG. 3B.

Example 8

3-Component Inhibition Fluorescence Assay

The fluorescence assay for characterizing pH-sensitive binding between bortezomib and catechol was carried out using procedures modified from the aforementioned literature method. Briefly, a solution of 0.1 mM ARS was prepared in 0.1 M phosphate monosodium buffer (solution A). Bortezomib was dissolved in solution A to achieve final concentration of 1 mM (solution B). The pH of both solution A and solution B was adjusted to 5.5, 6.5 and 7.4 using a 4N NaOH aqueous solution. Solution B was titrated to solution A to make a series of solutions that contain constant concentration of ARS (0.1 mM) and varying concentration of bortezomib (0~1 mM) at defined pH. After mixing the two solutions, the final solution stood for 5 minutes before fluorescence measurement at excitation 495 nm, emission 565 nm on SpectraMax M5 (Molecular Devices, Sunnyvale, Calif.). This procedure was used to probe the pH-dependence of ARS-BTZ binding (FIG. 6). The binding capacity of catechol for bortezomib was characterized based on the inhibition of catechol on ARS-bortezomib binding, resulting in a decrease in fluorescence intensity. For this competitive inhibition assay, 2 separate solutions in 0.1 M phosphate monosodium buffer were prepared: solution C containing 0.1 mM ARS and 1 mM bortezomib and solution D containing 0.1 mM ARS, 1 mM bortezomib and 10 mM PEG-Cat. Solution D was titrated to the solution C to make a series of solutions that contain constant concentrations of ARS (0.1 mM) and bortezomib (1 mM) but varying concentration of compound 1 (0~10 mM) separately at pH 5.5, 6.5 and 7.4. Fluorescence intensity of each solution was measured to plot the binding inhibition curves in FIG. 7. The following equation was used to convert fluorescence inhibition to relative binding affinity of PEG-Cat for BTZ in FIG. 2C: Binding Affinity $\% = (F_{max} - F_c)/F_{max} \times 100\%$. Fmax refers to the fluorescence intensity of ARS-BTZ conjugate in solution C at a defined pH. Fc refers to the fluorescence intensity of ARS-BTZ conjugate with PEG-Cat of specific concentration (in the range of 0~10 mM) at a defined pH.

Example 9

The amphiphilicity of BPC gave micelle-like structures in the range of 30~50 nm in diameter in aqueous solutions (pH 7.4), and the size of microstructure increased to 50~80 nm after the conjugation of BTZ.

Example 10

Cell Culture and Biotin-Mediated Cell Uptake of PEG-FITC

MDA-MB-231 breast cancer cells was originally purchased from ATCC and cultured in MEM containing 10 mM L-glutamine, nonessential amino acids, 10 mM HEPES, 100 U/ml streptomycin, 100 U/ml penicillin and 10% FBS at 37° C. under 5% $CO_2$. Passages between 9 and 12 were used for all the cell experiments. MCF-10A-Vector and MCF-10A-H-Ras cells were cultured in DMEM-F12 media supplemented with 20 ng/ml EGF, 10 µg/ml insulin, 0.5 µg/ml hydrocortisone, 100 ng/ml cholera toxin, 100 U/ml streptomycin, 100 U/ml penicillin and 5% FBS. Cells were seeded in 24-well plates at a density of $1 \times 10^5$ cells/ml and cultured for 24 hours. Cells were washed with PBS containing 0.91 mM $Ca^{2+}$ and 0.56 mM $Mg^{2+}$ and treated with solutions of 1 µM compound 2 or 3 in PBS for 15 minutes at 37° C. Cells treated with PBS only were used as control. Varying concentrations of biotin in buffer were used to inhibit the cellular uptake of biotin-PEG-FITC. Cells were then washed with PBS and imaged under an Eclipse TE2000U inverted fluorescence microscope at 10× magnification (FIGS. 8A-D and 9).

Example 11

Preparation of Catechol-Containing Polymer-Bortezomib Conjugates for Cytotoxicity For all the experiments where polymer-bortezomib conjugates were tested, the following sample preparation method was used. Bortezomib and catechol-containing polymers including were separately dissolved in DMSO at 0.1 M. Bortezomib-polymer conjugates were prepared by mixing solutions of 0.1 M bortezomib and 0.1 M PC or BCP in DMSO at volume ratio 4:1. These stock solutions were then diluted in PBS (containing $Ca^{2+}$ and $Mg^{2+}$) to achieve a 0.1 mM concentration of each compound. Solutions of bortezomib, polymers and bortezomib-polymer conjugates were further diluted with the cell assay buffer (serum-free cell growth buffer) to obtain final solutions used in cytotoxicity studies.

Example 12

Proteasome activity assay. MDA-MB231 breast carcinoma cells were seeded in 96-well plates at $1 \times 10^5$ cells/ml and cultured for 24 hours. Cells were washed with PBS and treated with solutions of bortezomib, catechol-containing polymers and polymer-bortezomib conjugates at defined concentrations for 2 and 6 hours at 37° C. under 5% $CO_2$. Cells treated with the assay buffer only were used as control. Cells were then washed with PBS and treated with reagents from a proteasome activity assay kit (Cayman Chemicals, Ann Arbor, Mich.) following the manufacture's protocols. The fluorescence measurement was carried out at excitation 360 nm, emission 480 nm.

Example 13

Cell Viability Assays

MDA-MB231 cells were seeded in 96-well plates at 3,000 cells/well and cultured for 24 hours. Cells were washed with PBS and treated with solutions of bortezomib, catechol-containing polymers and polymer-bortezomib conjugates at defined concentrations in cell growth media containing 1% serum for 48 hours at 37° C. under 5% $CO_2$. Cells treated with the assay buffer only were used as control. Cells were then washed with PBS and cell viability was analyzed using a commercial cell live/dead assay kit (live cells stained as green and red cells stained as red) followed by calculation of cell death using the following equation to plot data for FIG. 5. Cell death %=number of dead cells/(total number of live and dead cells)×100%.

Example 14

Cell Apoptosis Assays

Cell apoptosis and necrosis were measured by fluorescence-activated cell sorting (FACS) using Annexin-V, Alexa Fluor 67 conjugate (Invitrogen) as apoptosis indicator and 4',6-diamindino-2-phenylindole (DAPI) as a dead-cell indicator, following manufacturer's protocol. MCF-10A vector and MCF-10A-H-RasV12 cells were treated with BPC-BTZ (10 or 25 nM), BPC (25 nM) and media only for 48 h prior to analysis at the Robert H. Lurie Cancer Center Flow Cytometry Core Facility. The data were plotted with red dots representing histogram of cells that exhibit a particular combination of Annexin-V/DAPI fluorescence. (FIG. 10.)

Example 15

Cell Proliferation Assays

MCF-10A vector and MCF-10A-H-RasV12 cells were seeded in 96-well plates at 10,000 cells/well and cultured for 24 hours. The media in the wells were then replaced with a prepared growth media containing bortezomib, catechol-containing polymers and polymer-bortezomib conjugates at defined concentrations in DMEM-F12. Treated cells were further incubated for 48 hours at 37° C. under 5% $CO_2$. Cells were then washed with PBS and cell survival was determined by MTS assay, and the relative cell survival percentages compared to the drug-free control were plotted against the total BTZ concentration in logarithmic scale. The dose-response curves were obtained using (FIG. 11) sigmoldal logistic fitting (SigmaPlot version 10) to calculate the half-maximal inhibitory concentration ($IC_{50}$) values presented in FIG. 5C.

The polymeric drug delivery system of this invention, based on catechol-boronic acid dynamic binding, is a new addition to conventional pH-sensitive drug delivery systems. In particular and as contrasted with systems of the prior art, this invention provides a chemically-defined and tunable mechanism for drug loading and release, which permits high reproducibility and flexibility for various applications. Further, variation of the targeting ligand can be used to change the site of drug delivery from one tissue environment to another. Because boronic acid structures exists in many chemotherapeutics and other therapeutics for treating various types of diseases (e.g., Yang, W.; Gao, X.; Wang, B. Medicinal Research Reviews 2003, 23, 346; Minkkilä; A.; Saario, S. M.; Käsnänen, H.; Leppänen, J.; Poso, A.; Nevalainen, T. Journal of Medicinal Chemistry 2008, 51, 7057; and Kong, Y.; Grembecka, J.; Edler, M. C.; Hamel, E.; Mooberry, S. L.; Sabat, M.; Rieger, J.; Brown, M. L. Chemistry & Biology 2005, 12, 1007), such a targeted drug delivery approach can have wide application in both basic and applied biomedical programs.

We claim:

1. A compound comprising a poly(alkylene oxide) component; and a component of repeating lysine monomeric units coupled thereto, each said lysine monomeric unit coupled to a catecholic component, each said catecholic component pendant to a said lysine monomeric unit and conjugated with a bortezomib component, said conjugation via a dihydroxyphenyl moiety of said catecholic component and a boronic acid moiety of said bortezomib component, or a salt of said compound.

2. The compound of claim 1 wherein each said poly(alkylene oxide) component comprises poly(ethylene oxide).

3. The compound of claim 1 wherein said poly(alkylene oxide) component comprises about 30-about 250 repeating monomeric ethylene oxide units.

4. The compound of claim 3 comprising up to about 8 catecholic components.

5. The compound of claim 1 comprising a cancer cell-targeting ligand, said compound in a pharmaceutical composition.

* * * * *